US00PP11244P

United States Patent [19]

Bull

[11] Patent Number: Plant 11,244

[45] Date of Patent: Feb. 29, 2000

[54] NEW GUINEA IMPATIENS PLANT NAMED 'ARABELLA'

[76] Inventor: Norbert Bull, Gaertnersiedlung 2, 24610 Goennebek, Germany

[21] Appl. No.: 08/881,086

[22] Filed: Jun. 23, 1997

[51] Int. Cl.[7] ..... A01H 5/00

[52] U.S. Cl. ..... Plt./318

[58] Field of Search ..... Plt./87.6, 318

[56] References Cited

U.S. PATENT DOCUMENTS

P.P. 8,360 8/1993 Bull ..... Plt./87.6

*Primary Examiner*—Howard J. Locker
*Assistant Examiner*—Kent L. Bell
*Attorney, Agent, or Firm*—Foley & Lardner

[57] ABSTRACT

A new and distinct cultivar of New Guinea Impatiens plant named 'Arabella', characterized by its salmon orange flower color, large, generally round flowers, medium green foliage which is without variegation and which is narrow and elliptical in shape; short, relatively weak growth plant habit, and early to medium flowering response.

1 Drawing Sheet

The present invention comprises a new and distinct cultivar of New Guinea Impatiens, referred to by the cultivar name 'Arabella'.

'Arabella' is a product of a planned breeding program and was originated from a hybridization made by the inventor Norbert Bull in a controlled breeding program in Goennebek, Germany, in 1994. The female parent was seedling designated no. 5 and the male parent was a seedling designated no. 1. Both parents are proprietary cultivars used in the breeding program.

'Arabella' was discovered and selected as one flowering plant within the progeny of the stated cross by the inventor in 1995 in a controlled environment in Goennebek, Germany.

The first act of vegetative or asexual reproduction of 'Arabella' was accomplished when cuttings were taken from the initial selection in Autumn 1995 in a controlled environment in Goennebek by, or under the supervision of, Norbert Bull.

Horticultural examination of plants grown from these cuttings initiated in Spring 1996 in Goennebek, Germany, and continuing thereafter, has demonstrated that the combination of characteristics as herein disclosed for 'Arabella' are firmly fixed and are retained through successive generations of asexual reproduction.

'Arabella' has not been observed under all possible environmental conditions. The phenotype may vary significantly with variations in enviroment such as temperature, light intensity and day length, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Arabella', which in combination distinguish this impatiens as a new and distinct cultivar:

1. Salmon orange flower color
2. Large, round shaped flowers
3. Medium green foliage, narrow elliptically shaped
4. Short and relatively weak growing plant habit
5. Early to medium flowering response
6. Resistant to powdery mildew Of the many commercial cultivars known to the present inventor, the most similar in comparison to 'Arabella' is the cultivar 'BSR-195 Salmon' (U.S. Plant Pat. No. 8,870). In comparison to 'BSR-195 Salmon', the flowers of 'Arabella' are slightly smaller and have a more orange hue (R.H.S. 43 B compared to R.H.S. 46 C–D for 'BSR-195 Salmon'), and although its leaves are similar in shape to the leaves of 'BSR-195 Salmon', the leaf color is a uniform medium green without variegation.

The accompanying colored photographic drawing shows typical flower and foliage charactertistics of 'Arabella', with colors being as true as possible with illustrations of this type.

In the following description color references are made to The Royal Horticultural Society Colour Chart.

The color values were determined indoors from flowers taken from plants grown in Hillscheid, Federal Republic of Germany, under greenhouse conditions which approximate those generally used in commercial practice.

The description is based on plants which were planted as rooted cuttings in 10 cm pots in early March and then grown in a greenhouse at 20° C. minimum temperature.

Classification:

*Botanical.*—A hybrid of the genus Impatiens.

*Commercial.*—New Guinea Impatiens cv 'Arabella'.

PLANT

A. General appearance and form:

*Habit.*—Moderately compact, medium sized, low, rounded shape, well-branched, the growth is indeterminate, though weak after flowering begins.

*Height.*—11 cm.

*Width.*—25 cm.

*Internode length.*—20–30 mm.

*Stem color.*—Mainly green, reddish pink near the nodes.

*Flowering response.*—7–8 weeks (early to medium).

*Natural flowering season.*—Generally indeterminate, mainly from March to October, depending on light intensity.

*Propagation.*—Usually terminal tips as cuttings.

*Rooting.*—About 18 days at 22° C. from sticking to transplanting.

B. Foliage:

*Leaf arrangement.*—Primarily in whorls.

*Shape of leaf.*—Narrow elliptic, with acute base, and slightly acuminate tip.

*Margin.*—Slightly serrated, ciliated.

*Leaf, length.*—120 mm.

*Leaf, width.*—Narrow 33–37 mm.

*Main color of upper surface.*—Medium to dark green, approximately R.H.S. 137 A–B.

*Veins on upper surface, color.*—Light green.

*Variegation on leaf.*—Absent.

*Main color of lower surface.*—Light green, about R.H.S. 138 B.

*Veins on lower surface, color.*—Greenish white.

*Petiole, length.*—About 15 mm.

*Petiole, color.*—Brownish pink.

INFLORESCENCE

A. Flower:

*Number of flowers per node.*—About 5–7 in various stages of development, up to five open flowers at the same time, thus appearing floriferous, flowers are borne well above the foliage.

*Form of corolla.*—Single, 5 petals.

*Shape.*—Relatively large, outline nearly round, not quite closed — with gaps between the upper petal and the lower petals, flowers are usually flat and borne well above the foliage.

*Average length.*—68–70 mm.

*Average width.*—65–70 mm.

*Shape of petals.*—Cordate, moderately lobed, and occasionally slightly folded along the middle line.

*Petal, width.*—Up to 40 mm for the upper petal. About 28 mm for the lower petals.

*Petal, texture.*—Smooth, slightly glossy.

*Color* (*general tonality from a distance of three meters*) .—Orange-red.

*Main color of upper surface.*—R.H.S. 43 B.

*Color of lower surface.*—R.H.S. 41 A.

*Eye zone.*—Hardly visible, very slight pink hue.

*Spur, color.*—Brownish orange, R.H.S. 47 A.

*Spur, shape.*—Downwardly curved.

*Spur, size.*—45 mm long.

*Pedicel, color.*—Light green, R.H.S. 144 C.

*Pedicel, length.*—40–45 mm, relatively long.

B. Reproductive organs:

*Androecium.*—Stamens: 5, fused, upper surface light red, about R.H.S. 43 C. Anthers: hooded, yellowish white, R.H.S. 11 D. Pollen: yellowish white, about R.H.S. 4 D.

*Gynoecium.*—Stigma and style: 5, very short, light, R.H.S. 11 D. Ovary: 5-celled, 5 mm in length, surface medium green R.H.S. 137 B.

I claim:

1. A new and distinct cutlivar of New Guinea Impatiens plant named ‘Arabella’, as illustrated and described.

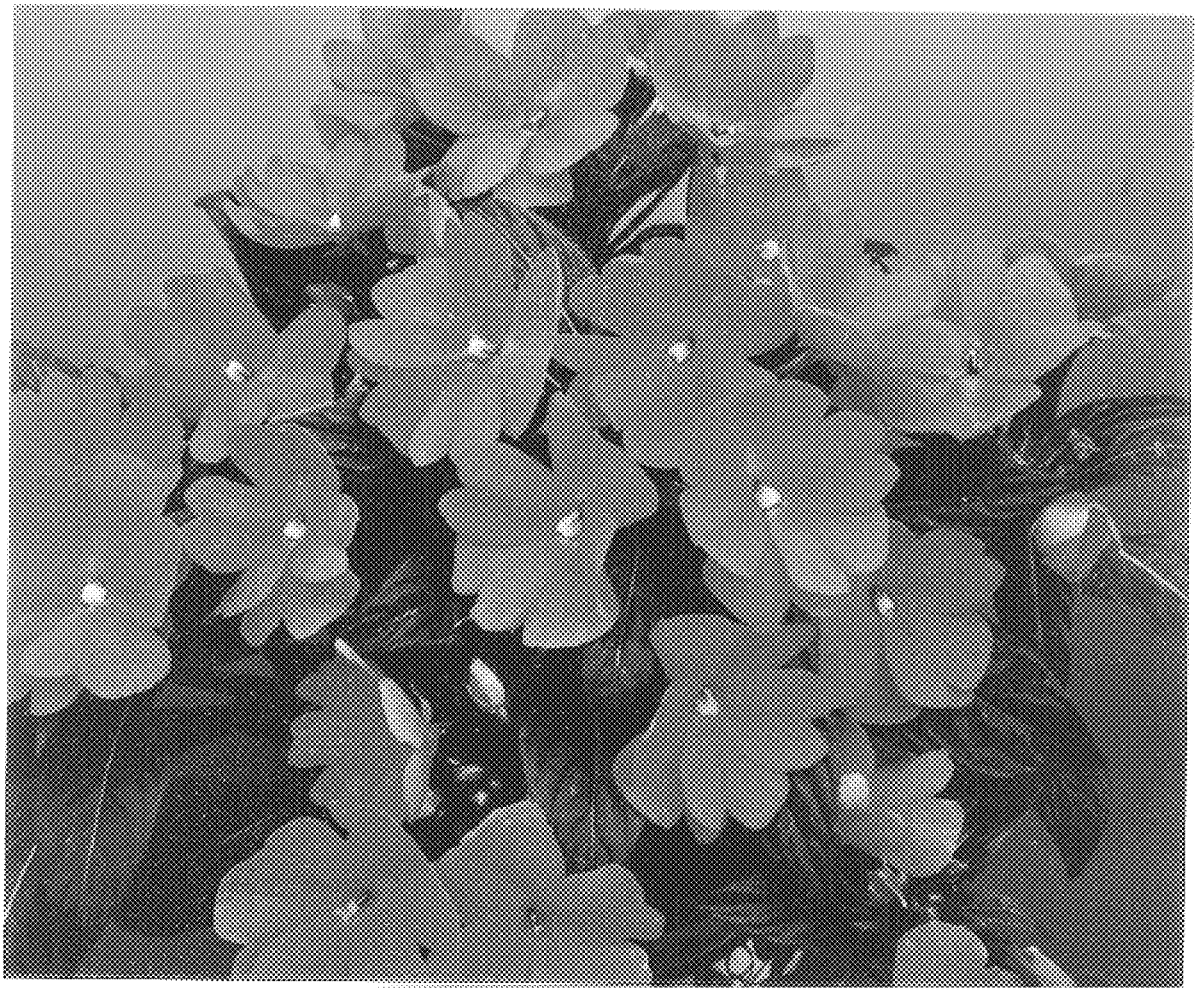

* * * * *